United States Patent
Wu et al.

(10) Patent No.: US 9,387,257 B2
(45) Date of Patent: Jul. 12, 2016

(54) LUNG CANCER SPECIFIC PEPTIDES FOR TARGETED DRUG DELIVERY AND MOLECULAR IMAGING

(71) Applicant: Academia Sinica, Taipei (TW)

(72) Inventors: Han-Chung Wu, Taipei (TW); Yi-Hsuan Chi, Tainan (TW)

(73) Assignee: ACADEMIA SINICA, Taipei (TW)

( * ) Notice: Subject to any disclaimer, the term of this patent is extended or adjusted under 35 U.S.C. 154(b) by 16 days.

(21) Appl. No.: 14/599,291

(22) Filed: Jan. 16, 2015

(65) Prior Publication Data

US 2015/0202316 A1    Jul. 23, 2015

Related U.S. Application Data

(60) Provisional application No. 61/928,507, filed on Jan. 17, 2014.

(51) Int. Cl.
| | |
|---|---|
| *A61K 38/16* | (2006.01) |
| *C07K 5/00* | (2006.01) |
| *A61K 47/48* | (2006.01) |
| *A61K 31/704* | (2006.01) |
| *G01N 33/574* | (2006.01) |

(52) U.S. Cl.
CPC ......... *A61K 47/48246* (2013.01); *A61K 31/704* (2013.01); *A61K 47/48815* (2013.01); *G01N 33/57423* (2013.01); *G01N 2458/00* (2013.01)

(58) Field of Classification Search
None
See application file for complete search history.

(56) References Cited

U.S. PATENT DOCUMENTS

2009/0111845 A1*  4/2009  Cao .............................. 514/283
2010/0017904 A1*  1/2010  Abad ................... C07K 14/415
                                                    800/270

OTHER PUBLICATIONS

Fields et al. Food Chemistry 134 (2012) 1831-1838.*
Peng et al. Int J Nanomedicinev.3(3); Sep. 2008, PMC2626938.*
Hsiung et al (2008). Detection of colonic dysplasia in vivo using a targeted heptapeptide and confocal microendoscopy. Natural Medicine, 14(4), 454-458.
Kimberly A. Kelly and David A. Jones (2003). Isolation of a Colon Tumor Specific Binding Peptide Using Phage Display Selection. Neoplasia, 5(5), 437-444.
Rasmusssen et al. (2002). Tumor cell-targeting by phage-displayed peptides. Cancer Gene Therapy, 9, 606-612.

* cited by examiner

*Primary Examiner* — Jeanette Lieb
(74) *Attorney, Agent, or Firm* — Hsiu-Ming Saunders;Intellectual Property Connections, Inc.

(57) ABSTRACT

A conjugate is disclosed. The conjugate comprises (a) an isolated or a synthetic targeting peptide of less than 15 amino acid residues in length, comprising an amino acid sequence having at least 90% identity to a sequence selected from the group consisting of SEQ ID NOs: 1-8; and (b) a component conjugated to the targeting peptide, the component being selected from the group consisting of a drug delivery vehicle, an anti-cancer drug, a micelle, a nanoparticle, a liposome, a polymer, a lipid, an oligonucleotide, a peptide, a polypeptide, a protein, a cell, an imaging agent, and a labeling agent. Methods of treating lung cancer and detecting lung cancer cells are also disclosed.

20 Claims, 9 Drawing Sheets

FIG. 1A
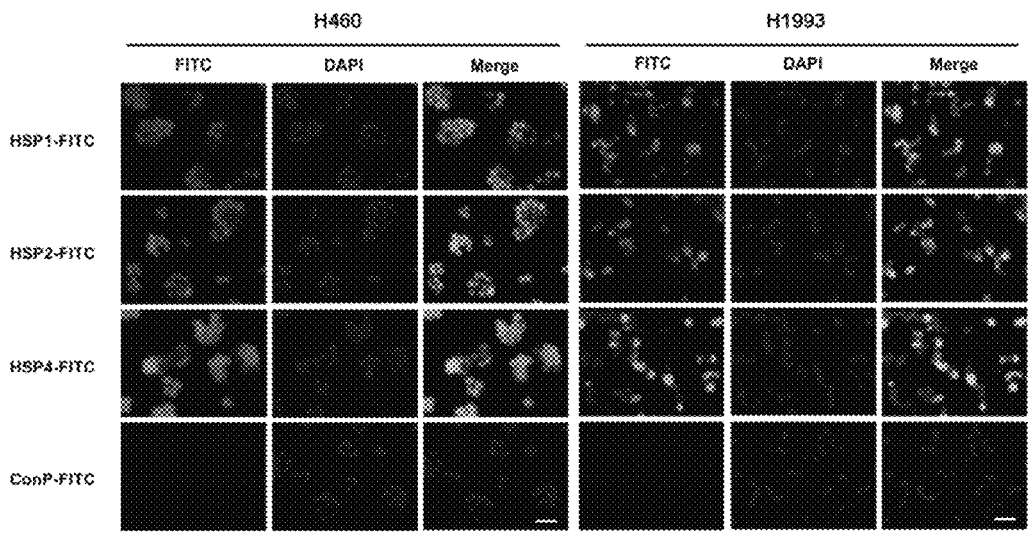
FIG. 1B
| IFA Positive Cells (%) | | | |
|---|---|---|---|
| | HSP1-FITC | HSP2-FITC | HSP4-FITC |
| H460 | 77.01 % | 76.5 % | 83.22% |
| H1993 | 66.94 % | 61.11 % | 55.93% |
FIG. 2B
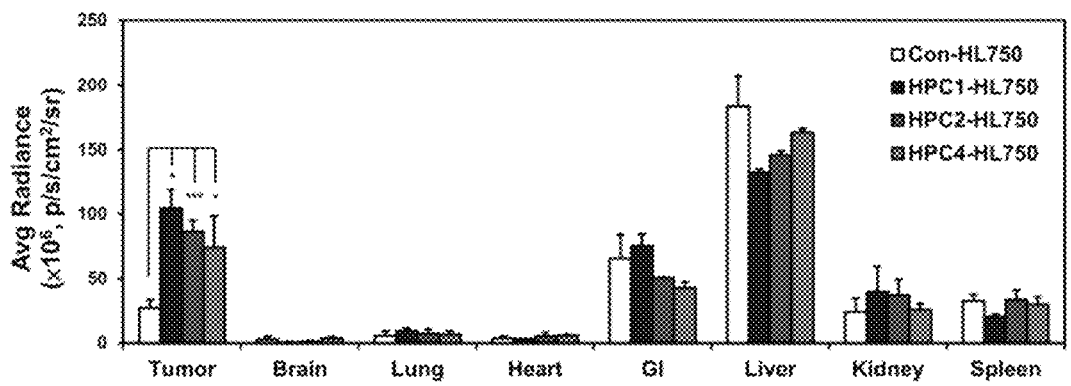

| Median survival time (days) | |
|---|---|
| PBS | 51 |
| FD + FV | 55 |
| LD + LV | 63 |
| HSP4-LD + HSP4-LV | 74 |

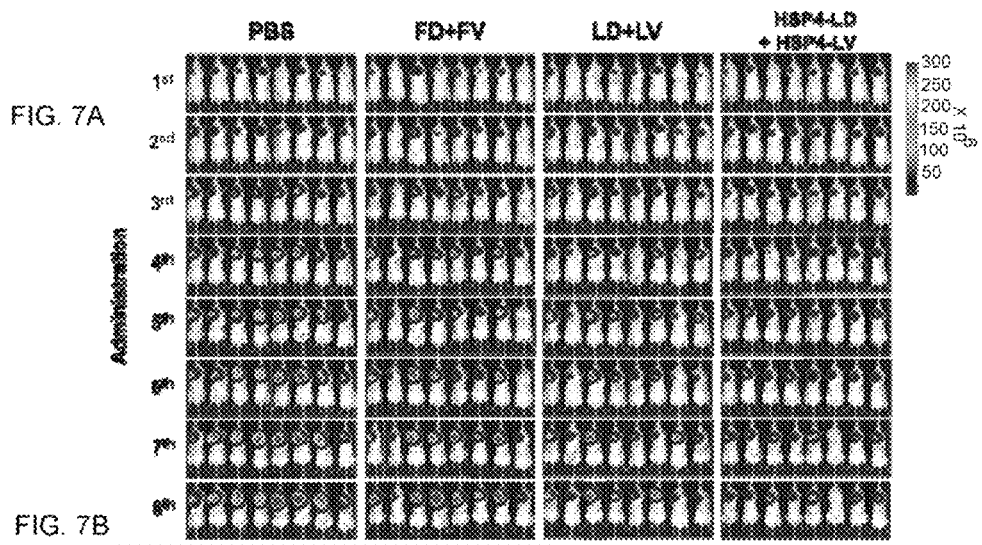
FIG. 7A
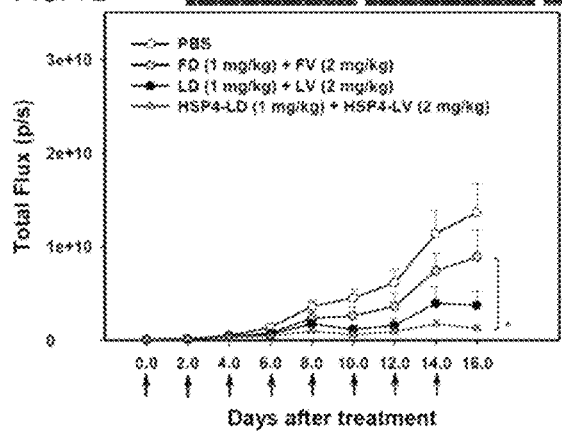
FIG. 7B
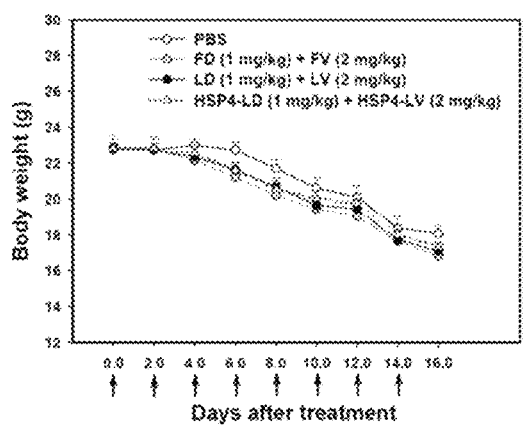
FIG. 7C
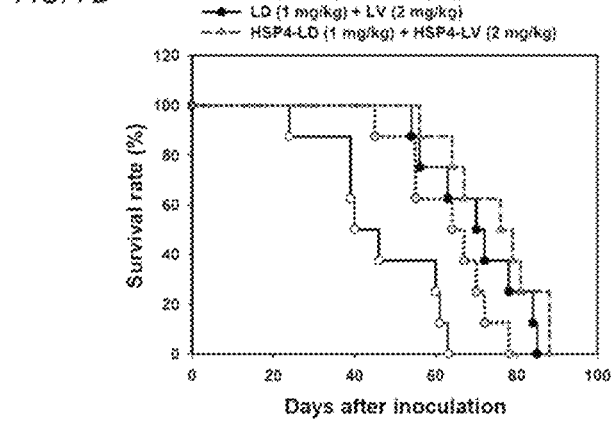
FIG. 7D
FIG. 7E
| Median survival time (days) | |
|---|---|
| PBS | 43 |
| FD + FV | 65.5 |
| LD + LV | 71 |
| HSP4-LD + HSP4-LV | 77.5 |

FIG. 8A
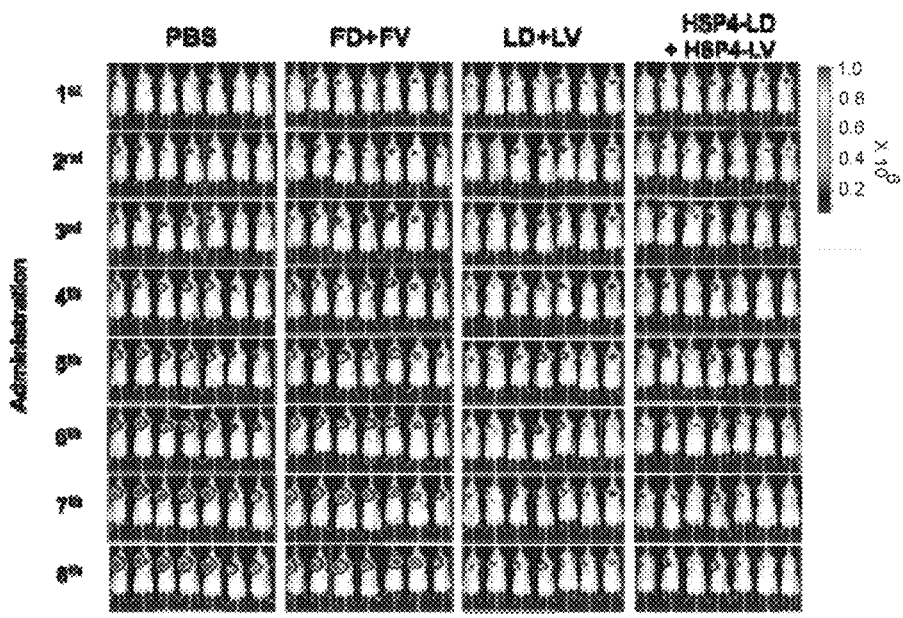
FIG. 8B
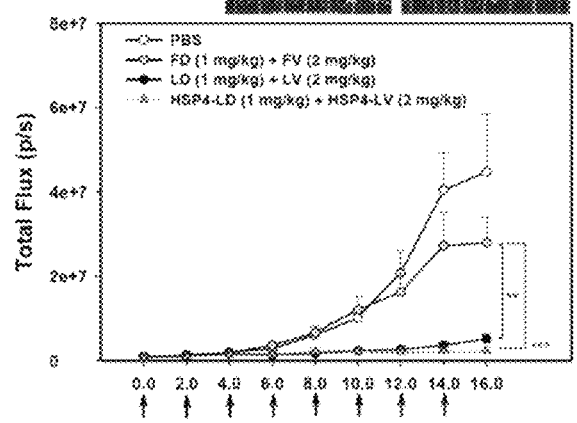
FIG. 8C
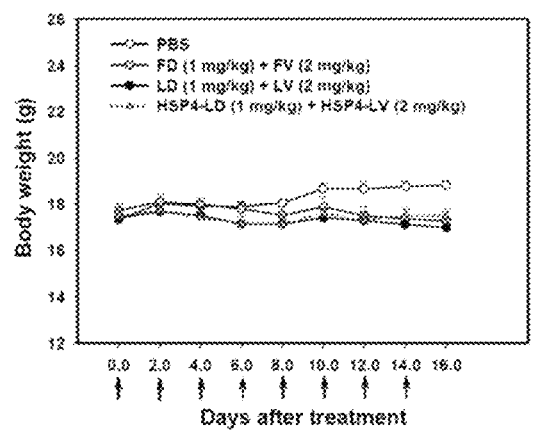
FIG. 8D
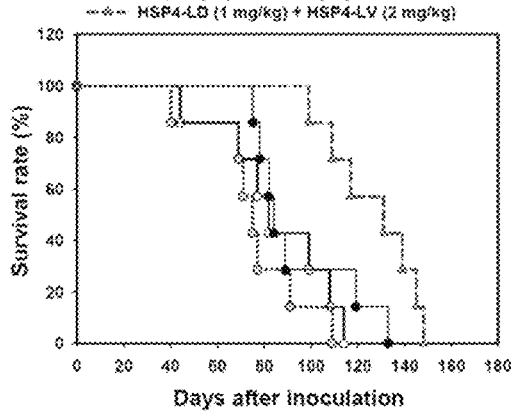
FIG. 8E
| Median survival time (days) | |
|---|---|
| PBS | 82 |
| FD + FV | 75 |
| LD + LV | 84 |
| HSP4-LD + HSP4-LV | 131 |

# LUNG CANCER SPECIFIC PEPTIDES FOR TARGETED DRUG DELIVERY AND MOLECULAR IMAGING

REFERENCES TO RELATED APPLICATION

The present application claims priority to U.S. Provisional Application Ser. No. 61/928,507, filed Jan. 17, 2014, which is herein incorporated by reference in its entirety.

FIELD OF THE INVENTION

The present invention relates generally to a drug delivery system, and more specifically to a lung cancer targeted drug delivery system.

BACKGROUND OF THE INVENTION

Lung cancer is the leading cause of cancer-related mortality in both men and women. An estimated 159,480 deaths have occurred in the U.S. in 2013, accounting for about 27% of all cancer deaths. Lung cancer can be histopathologically classified as small cell (15%) or non-small cell (84%) for the purposes of treatment, with the latter consisting of large cell carcinoma (LCC), adenocarcinoma and squamous cell carcinoma (SCC). Although surgery, radiotherapy, chemotherapy, and even EGER targeted therapies such as cetuximab (Erbitux), erlotinib (Tarceva), and gefitinib (Iressa) have been used to treat different stages or types of lung cancer, the 5-year survival rates for small cell carcinoma (SCLC) and non-small cell lung carcinoma (NSCLC) remain low, at 6% and 18%, respectively.

One major cause for this disappointing outcome is lack of selectivity for conventional chemotherapeutics in cancer treatment, which results in a narrow therapeutic window and severe damage to normal tissues. The other reason is high interstitial fluid pressure (IFP) of solid tumors which makes it difficult for anticancer agents or even small molecular tyrosine kinase inhibitors commonly used in targeted therapy to enter into the tumor site. It has been shown that the amount of drug accumulated in normal viscera is ~10- to 20-fold higher than that in the same weight of tumor site, and that many anticancer drugs are not able to penetrate more than 40-50 μm (equivalent to the combined diameter of 3-5 cells) from the vasculature. These deficiencies often lead to limited therapeutic function and multiple drug resistance, thereby compromising clinical prognosis.

SUMMARY OF THE INVENTION

In one aspect, the invention relates to a conjugate comprising:
 (a) an isolated or a synthetic targeting peptide of less than 15 amino acid residues in length, comprising an amino acid sequence having at least 90% identity to a sequence selected from the group consisting of SEQ ID NOs: 1-8; and
 (b) a component conjugated to the targeting peptide, the component being selected from the group consisting of a drug delivery vehicle, an anti-cancer drug, a micelle, a nanoparticle, a liposome, a polymer, a lipid, an oligonucleotide, a peptide, a polypeptide, a protein, a cell, an imaging agent, and a labeling agent.

The imaging agent may be iron oxide. The iron oxide may be encapsulated within a liposome.

The targeting peptide may comprise at least one motif selected from the group consisting of MHLXW, NPWXE, and WXEMM motifs, where X is any amino acid residue.

The conjugate as aforementioned may exhibit at least one of the following characteristics:
 (a) increased binding, to a lung cancer cell as compared to a control liposome;
 (b) enhanced endocytosis into a lung cancer cell as compared to a control liposome; and
 (c) decreasing the half maximal inhibitory concentration ($IC_{50}$) in cytotoxicity to a lung cancer cell;
 (d) enhancing efficacy of anticancer drugs in vivo;
 (e) decreasing a lung tumor size in vivo; and
 (f) prolonging an overall survival rate in a subject with a lung tumor.

In another aspect, the invention relates to an isolated or a synthetic targeting peptide of less than 15 amino acid residues in length, comprising an amino acid sequence having at least 90% identity to a sequence selected from the group consisting of SEQ. ID NOs: 1-8, wherein the isolated or the synthetic targeting peptide is active in, binding to a human lung cancer cell but not a normal cell. The lung cancer cell may be at least One selected from the group consisting of non-small cell lung cancer (NSCLC) and small cell lung cancer (SCLC). The lung cancer may be at least one selected from the group consisting of adenocarcinoma, papillary adenocarcinoma, bronchioloalveolar carcinoma, squamous cell carcinoma, large cell carcinoma, and small cell carcinoma.

In one embodiment of the invention, the isolated or a synthetic targeting peptide contains at least one substitution modification relative to the sequence selected from the group consisting of SEQ ID NO: 1-8.

In another embodiment of the invention, the isolated or a synthetic targeting peptide as aforementioned is conjugated to a component selected from the group consisting of a drug delivery vehicle, a liposome, a polymer, a lipid, a cell, an imaging agent, and a labeling agent.

The isolated or a synthetic targeting peptide may be conjugated to a PEG-phospholipid derivative, a liposome, or a PEGylated liposome. The PEG-phospholipid derivative may be selected from the group consisting of NHS-PEG-DSPE, PEG-DSPE.

The isolated or a synthetic targeting peptide may further comprise an anti-cancer drug or a fluorescent dye encapsulated within the liposome, or the PEGylated liposome.

Further in another aspect, the invention relates to a composition comprising:
 (a) liposomes or PEGylated liposomes; and
 (b) at least one isolated or one synthetic targeting peptide as aforementioned, conjugated to the surfaces of the liposomes or the PEGylated liposomes.

In one embodiment of the invention, the composition may comprises at least two isolated or synthetic targeting peptides conjugated to the surfaces of the liposomes of PEGylated Liposomes. Each of the liposomes or PEGylated liposomes may have a different targeting peptide conjugated thereto.

The composition may further comprises at least one anticancer drug encapsulated within the liposomes or PEGylated liposomes. The anticancer drug may be at least one selected from the group consisting of doxorubicin, and vinorelbine.

The composition may comprise one or more isolated or synthetic peptides as aforementioned.

In another embodiment of the invention, the composition comprises:
 (a) the isolated or synthetic peptide of SEQ ID NO: 3;
 (b) the isolated or synthetic peptide of SEQ ID NO: 1; or
 (c) the isolated or synthetic peptides of SEQ ID NO: 3 and SEQ. ID NO: 1.

Further in another aspect, the invention relates to a method of treating lung cancer, comprising administering to a subject in need thereof the composition as aforementioned.

Yet in another aspect, the invention relates to a method of detecting lung cancer cells, comprising:

(1) exposing the lung cancer cells to a conjugate comprising:
   at least one isolated or synthetic targeting peptide of claim 2; and
   an imaging agent or a labeling agent, conjugated to the at least one isolated or synthetic targeting peptide;
(2) removing the conjugate unbound to the lung cancer cells and detecting the imaging agent or the labeling agent conjugated to the isolated or a synthetic targeting peptide bound to the lung cancer cells; or
(i) exposing the lung cancer cells to a conjugate comprising:
   at least one isolated or synthetic targeting peptide of claim 2; and
   at least one phage, displaying at least one peptide on the surface thereof, the at least one peptide displayed on the phage has the amino acid sequence identical to the isolated or a synthetic targeting peptide of claim 2;
(ii) removing the conjugate unbound to the lung cancer cells and detecting the at least one phage bound to the lung cancer cells.

The cancer cells may be present in a tissue specimen, e.g., a surgical tissue specimen. One or more isolated or synthetic peptides as aforementioned may react and bind to a lung cancer tissue specimen.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIG. 1A shows immunofluorescent staining of FITC-labeled HSP1, HSP2, and HSP4 peptides to H460 large cell carcinoma and H1993 adenocarcinoma cell lines. Nuclear were stained by DAPI. Scale bar, 50 µm.

FIG. 1B is a table listing the percentage of IFA positive stained cells of HSP1, HSP2 and HSP4-FITC in H460 and H1993 cell lines.

FIGS. 2A-C show verifying the tumor homing ability of H460-targeting phages in vivo. (A) SCID mice bearing H460 xenografts were injected i.v. with selected phage clones. After 8 minutes, the free phages were washed out by PBS perfusion, then xenograft tumor masses and organs were removed for determination of phage titer (n=3). HPC2, 3 and 4 showed better tumor homing ability among four phage clones of group 1 with similar sequences, while HPC1 was the best in group 2. (B) Whole body imaging of HILYTE™ Fluor 750 labeled. HPC1, 2, 4 and control phage. The tissue distribution of these HILYTE™ Fluor 750 labeled phage were determined at 24 hr post-injection, and signal intensity of tumor and organs were measured by IVIS200 software. *, $P<0.05$; ***, $P<0.001$ (n=3). (C) The fluorescence images of the dissected organs from HPC1-HL750 injected mice were acquired and compared with control phage.

FIGS. 7A-E show HSP4-LD and HSP4-LV combination therapy to treat orthotopic model of H460 large cell carcinoma. (A) Imaging drug response of mice transplanted luciferase-expressing H460 cells to combination therapy with FD/FV, LD/LV, HSP4-LD/HSP4-LV at doses of ½ mpk or an equal volume of PBS intravenously. A total of 5×10⁵ cells were transplanted with MATRIGEL®, and the treatment started 4 days after cancer cells transplantation (once every two days for 8 times). n=8 in each group. (B) Luminescence signal of tumor were quantified using IVIS200 software. *, P<0.05. (C) Body weight change during the course of treatment. (D) A Kaplan-Meier survival curve and (E) median survival time of drug recipient mice.

FIGS. 8A-F show HSP4-LD and HSP4-LV combination therapy to treat orthotopic model of A549 adenocarcinoma. (A) Imaging drug response of mice transplanted luciferase-expressing A549 cells to combination therapy with FD/LV, LD/LV, HSP4-LD/HSP4-LV at doses of ½ mpk or an equal volume of PBS intravenously. A total of $5 \times 10^5$ cells were transplanted with MATRIGEL®, and the treatment started 5 days after cancer cells transplantation (once every two days for 8 times). n=7 in each group. (B) Luminescence signal of tumor were quantified using IVIS200 software. , P<0.01; *, P<0.001. (C) Body weight change during the course of treatment. The overall survival rate (D) and median survival days (E) were significantly prolonged by HSP4 targeting LD and LV.

DETAILED DESCRIPTION OF THE INVENTION

Figure 2A:
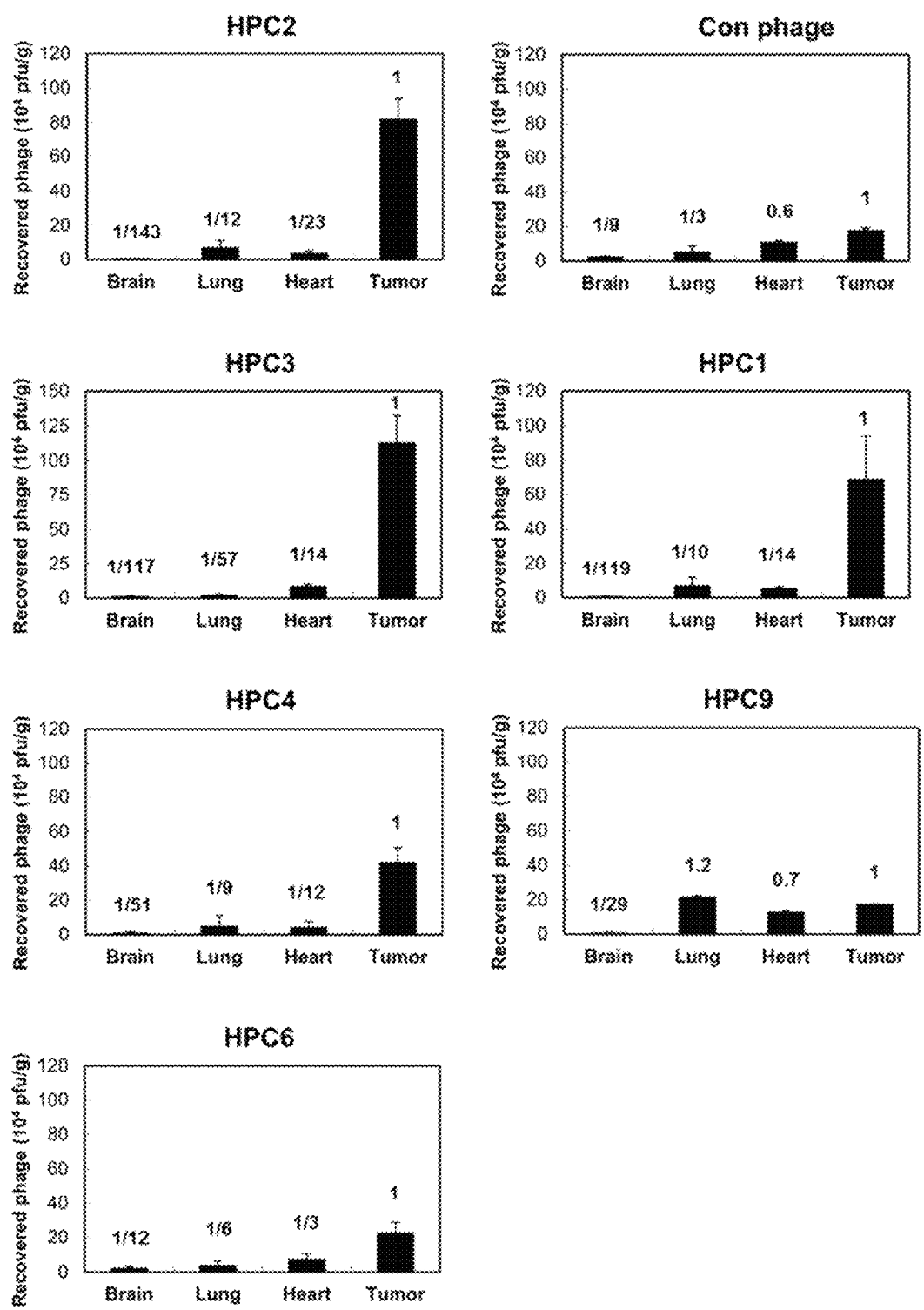

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise. Moreover, titles or subtitles may be used in the specification for the convenience of a reader, which shall have no influence on the scope of the present invention. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

The term "drug delivery vehicles" refers to a vehicle that is capable of delivering medication to a patient in a manner that increases the concentration of the medication in some parts of the body relative to others. Drug delivery vehicles includes, but not limited to, polymeric micelles, liposomes, lipoprotein-based drug carriers, nano-particle drug carriers, dendrimers, cells, polypeptides, etc. An ideal drug delivery vehicle must be non-toxic, biocompatible non-immunogenic, biodegradable, and must avoid recognition by the host's defense mechanisms. The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it Such a subject can be identified by a health care professional based on results from any suitable diagnostic method (see U.S. patent application Ser. No. 14/499,201, which is incorporated herein by reference in its entirety).

The term "treating" or "treatment" refers to administration of an effective amount of the compound to a subject in need thereof, who has cancer, or a symptom or predisposition toward such a disease, with the purpose of cure, alleviate, relieve, remedy, ameliorate, or prevent the disease, the symptoms of it, or the predisposition towards it. Such a subject can be identified by a health care professional based on results from any suitable diagnostic method.

The term "An effective amount" refers to the amount of an active compound that is required to confer a therapeutic effect on the treated subject. Effective doses will vary, as recognized by those skilled in the art, depending on rout of administration, excipient usage, and the possibility of co-usage with other therapeutic treatment.

The "Guidance for Industry and Reviewers Estimating the Safe Starting Dose in Clinical Trials for Therapeutics in Adult Healthy Volunteers" published by the U.S. Department of Health and Human Services Food and Drug Administration discloses a "therapeutically effective amount" may be obtained by calculations from the following formula:

$$HED = \text{animal dose in mg/kg} \times (\text{animal weight in kg/human weight in kg})^{0.33}.$$

In this study, we used a phage-displayed peptide library and biopanning technique to isolate lung cancer-specific peptides. We identified three novel peptides HSP1, HSP2 and HSP4 that were able to bind to several types of NSCLC (including LCC, adenocarcinoma, and SCC) and SCLC in both cell lines and clinical surgical specimens, but not normal pneumonic tissue. In vivo study further proved the enhanced therapeutic efficacy and bioavailability of these HSP1, 2, or 4 peptide-mediated drug delivery systems. These data demonstrated a promising potential for these three novel peptides in theranostics applications.

Iron oxide-binding peptides have been disclosed in U.S. Patent publication Nos. 20100158837 and US20090208420. Superparamagnetic iron oxide (USPIO)-based liposomes have been disclosed by Frascione D et al. (Int J Nanomedicine. 2012; 7:2349-59).

The term "a labeling agent" includes, but not limited to, "a fluorescent labeling agent".

Imaging agents are designed to provide more information about internal organs, cellular processes and tumors, as well as normal tissue They can be used to diagnose disease as well as monitor treatment effects.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Materials and Methods
Cell Lines and Cultures

NCI-H460, NCI-H661, NCI-H1993, NCI-H441, NCI-H520, NCI-H1688, A549 human lung cancer cell lines and NL20 human bronchial epithelial cells were purchased from American Type Culture Collection (ATCC®) and were authenticated by ATCC based on DNA profile, cytogenetic analysis and isoenzymology. These cells were cultured by ATCC's protocols and had been passaged for fewer than 6 months after resuscitation, CL1-5 cells were established and were verified routinely by growth, morphology and mycoplasma-free. The human normal nasal mucosal epithelial (NNM) cells were a primary culture derived from a nasal polyp and were grown in DMEM.

Phage Display Biopanning Procedures

Human lung large cell carcinoma cell line H460 cells were incubated with UV-treated inactive control helper phage (insertless phage). The phage-displayed peptide library, which initially contained $5 \times 10^{10}$ plaque-forming units (pfu) was then added. After washing, the bound phages were eluted with a lysis buffer (150 mM NaCl, 50 mM Tris-HCl, 1 mM EDTA, 1% NP-40, 0.5% sodium deoxycholate, 0.1% SDS, pH 7.4 on ice. This eluted phage pool was amplified and titered in an *Escherichia coli* ER2738 culture. Recovered phages were used as input for the next round of panning. In the fourth and fifth round of biopanning the phage clones were randomly selected to culture for ELISA screening (Manuscript submitted for publication, which is incorporated herein by reference in its entirety).

Identification of Phage Clones Using Cellular Enzyme-Linked Immunosorbent Assay (ELISA)

Ninety-six-well ELISA plates were seeded with either cancer or control NNM cells. Individual phage clones were added to the cell-coated plates and were incubated with horseradish peroxidase (HRP)-conjugated mouse anti-M13 monoclonal antibody, followed by incubating with the peroxidase substrate o-phenylenediamine dihydrochloride. The reaction was stopped and absorbance was measured at 490 nm using an ELISA reader. The selected phage clones were further analyzed using DNA sequencing with the primer 5'-CCCTCATAGTTAGCGTAACG-3' (SEQ ID NO: 12) corresponding to the pIII gene sequence.

Peptide Synthesis and Labeling

The synthetic targeting peptide HSP1 (GAMHLPWH-MGTL; SEQ ID NO: 1), HSP2 (NPWEEQGYRYSM; SEQ ID NO: 2), HSP4 (NNPWREMMYIEI; SEQ ID NO: 3) and control peptide (12 amino acid sequence from BSA protein, KATEEQLKTVME; SEQ ID NO: 13) were prepared by Fmoc SPPS using a CEM Liberty automated microwave peptide synthesizer and purified using reverse-phase high-performance liquid chromatography to 95% purity. Conjugation of these peptides with fluorescein isothiocyanate (FITC) was performed through the addition of FITC to the peptide C-terminus. Peptide synthesis, conjugation, and purification were performed by Peptide Synthesis Core Facility of the Institute of Cellular and Organismic Biology, Academia Sinica (Taipei, Taiwan).

Flow Cytometry Analysis

The lung cancer cell lines or control cells were collected using enzyme-free cell dissociation buffer, and then were incubated with 20 µg/mL FITC-conjugated HSP1, 2, 4 or control peptide at 4° C. for 1 hour. After washing, cells were analyzed by flow cytometer.

Immunofluorescence Staining of Synthetic Peptides to Lung Cancer Cells

H460 and H1993 cells were seeded and grown to about 50% confluence on cover slips. After the cells had been fixed with 2% paraformaldehyde, they were incubated with 10 µg/mL FITC-labeled HSP1, 2, 4 or control peptides. Then the slides were counterstained with 4',6-diamidino-2-phenylindole (DAPI), mounted and examined under a Leica universal fluorescent microscope. The images were merged using the MetaMorph Image Analysis Software.

Immunohisochemistry Staining for Human Surgical Specimens

Eleven cases of lung adenocarcinoma and ten cases of lung squamous cell carcinoma paraffin tissue section were obtained from tissue bank of National Taiwan University Hospital (NTUH) with approval from the Institutional Review Board in NTUH. To increase the case number and histopathological subtypes of lung cancer specimens, we also obtained commercial tissue microarray sections consisted of a total of 120 cases of lung adenocarcinoma, squamous cell carcinoma, large cell carcinoma, small cell carcinoma, etc. with approval of the AS-IRB03-102103. For localization of phages binding to the lung cancer tissues, the tissues were incubated with HPC1, HPC2, HPC4 or control phages ($2 \sim 5 \times 10^8$ pfu/µl). After washing with PBS, sections were treated with anti-M13 mouse mAb (GE Healthcare) for 1 hour at room temperature. Following washing steps, a biotin-free super sensitive polymer-HRP detection system was used to detect immunoreactivity. The slides were lightly counterstained with hematoxylin, mounted with AQUATEX® (Merck) and examined by light microscopy.

In Vivo Tumor Homing Assay and Imaging

SCID mice were injected subcutaneously in the dorsolateral flank with $5 \times 10^6$ H460 cells. The mice bearing size-matched lung cancer xenografts (approximately 300 mm$^3$) were intravenously injected with $2 \times 10^9$ pfu of the targeting phage or control phage. After eight minutes of phage circulation, the mice were sacrificed and perfused with 50 ml PBS to wash out unbound phage. Subsequently, xenograft tumors and mouse organs were dissected and homogenized. The phages bound to each tissue sample were recovered through the addition of ER2738 bacteria and titered on IPTG/X-Gal agar plates. For the in vivo whole body imaging, HPC1, 2, 4 and control phages were labeled with the fluorescence dye, HILYTE™ Fluor 750 acid NHS ester (HL750), by NHS functional group. Same H460 xenograft model were intravenously injected with $5 \times 10^9$ pfu of the HL750-labeled targeting phages or control phages. Fluorescence imaging of mice and tissues was captured using Xenogen IVIS200 imaging system (Excitation 710/760 nm; Emission: 810/875 nm) at indicated time points. And the fluorescence intensity of tissues was calculated by subtracting background using Living Image software (Xenogen).

Preparation of Synthetic Peptide-Conjugated Liposomal Doxorubicin, Vinorelbine and SRB The peptide was coupled to NHS-PEG-DSPE [N-hydroxysuccinimido-carboxyl-polyethyleneglycol (MW, 3400)-derived distearoylphosphatidyl ethanolamine] in a 1.1:1 molar ratio. The PEGylated peptide-PEG-DSPE conjugates were purified by SEPHADEX® G-15 (GE healthcare) gel filtration chromatography, and were then dried through lyophilization. The conjugates were also analyzed by HPLC quantitatively and by MALDI-TOF-MS (BRUKER MICROFLEX™) qualitatively.

A lipid film hydration method was used to prepare PEGylated liposomes composed of distearoylphosphatidylcholine, cholesterol, and PEG-DSPE, which were then used to encapsulate doxoruhicin, vinorelbine or to incorporate sulforhodamine B-DSPE with the particle size ranging from 65 to 75 nm in diameter. HSP1, 2, or 4-PEG-DSPE was subsequently incorporated into pre-formed liposomes by co-incubation at 60° C., the transition temperature of the lipid bilayer, for 1 hour with gentle shaking. After incubation, the surface of each liposome displayed about 500 peptide molecules. SEPHADEX™ G-25 gel filtration chromatography was used to remove released free drug, unconjugated peptides, and unincorporated conjugates. Doxorubicin and vinorelbine concentrations m the fractions of eluent were determined by measuring Excitation/Emission wavelengths of fluorescence at 485/590 and 520/570 nm, respectively, using spectrofluorometer (Spectra Max M5, Molecular Devices).

Uptake of Targeting Peptide-Conjugated LSRB or LD by Human Lung Cancer Cells

H460 and H1993 cells were grown on a 24-well plate to 90% confluency, and 20, 10, 5, 2.5, 1.25, 0.625 µM HSP1, 2, 4-liposomal sulforhodamine B (LSRB) or LSRB in complete culture medium was added. The cells were incubated at 37° C., at the following time periods: 10, 30 min, 1, 2, 4, 8, 16 and 24 hours. At the indicated time point, cells were washed with PBS, and non-internalized LSRB on the cell surface was removed by adding 0.1 M Glycine, pH 2.8 for 10 min. Cells were then lysed with 200 µl 1% Triton X-100. Uptake of LD at low concentration in H1993 cells was performed using same protocol. For extraction of SRB or doxorubicin, 300 µl IPA (0.75 N HCl in isopropanol) was added to the lysate and shaken for 30 min. After the lysate was centrifuged at 12,000 rpm for 5 min, the amount of uptakes were determined by measuring Excitation/Emission wavelengths of fluorescence at 520/570 nm for SRB and 485/590 nm for doxorubicin using, a spectrofluorometer (SPECTRAMAX® M5, Molecular Devices). The concentration of SRB and doxambicin were calculated by interpolation using a standard curve.

Endocytosis Assay

H460 cells were incubated with HSP1, HSP2, HSP4-LSRB or LSRB for 10 min at 4° C. and 37° C. After being washed with PBS, the cells were fixed by 4% paraformaldehyde, blocked by 1% BSA, and then stained with WGA-ALEXA FLUOR® 467 and DAPI for cell membrane and nucleus. All fluorescence images were obtained by confocal microscopy.

In Vitro Cytotoxicity Assay of Targeting Peptide-Conjugated LD

H460 cells were seeded in 96-well plates (5000 cells/well) in complete culture media and were incubated overnight. Next day, cells were treated with varying concentration (0~100 µM) of HSP1-LD, HSP2-LD, HSP4-LD or LD at 37° C. for 24 hours; After removal of the excess drug, the cells were washed once with PBS and continued to incubate with fresh culture medium for 48 h at 37° C. The cell viability was measured by adding 50 µl of MTT (Thiazolyl Blue Tetrazolium Bromide; Sigma-Aldrich) to each well of the plate. After 3.5 hours MTT incubation, 150 µl of Dimethyl sulfoxide (DMSO; Mallinckrodt Baker) was added to each well for 10 min, and the absorbance was determined with microplate reader (SPECTRAMAX® M5, Molecular Devices) at 540 nm.

Animal Models for the Study of Ligand-Targeted Therapy

Female SCID mice 4-6 weeks of age were injected subcutaneously in the dorsolateral flank with human NSCLC cells. Mice with size-matched tumors (approximately 75 mm$^3$ for small tumor; 300 or 500 mm$^3$ for large tumor) were then randomly assigned to different treatment groups, and were injected intravenously with liposomal doxorubicin (LD), liposomal vinorelbine (LV), targeting peptide (HSP1, HSP2 or HSP4)-conjugated LD or LV, free doxorubicin (FD), free vinorelbine (FV) or equivalent volumes of saline. The dosages of drugs and administration time courses were described in figure legends depend on different experiment design. Mouse body weights and tumor sizes were measured twice a week. Tumor volumes were calculated according to this formula: length×(width)$^2$×0.52. Animal care was carried out in accordance with guidelines of Academia Sinica, Taipei, Taiwan. The protocol was approved by the Committee on the Ethics of Animal Experiments of Academia Sinica.

Orthotopic Lung Cancer Models

SCID mice (6-week-old) were anesthetized with isofloruance mixed with oxygen and placed in the right decubitus position. The skin overlying the left chest wall in the midaxillary line was prepared with alcohol, and the underlying, chest wall and intercostal spaces were visualized. Luciferase-overexpressed H460 or A549 cells ($5 \times 10^5$ cells) in 50 µl serum-free medium plus MATRIGEL® Matrix (2:1) were injected into the left lateral thorax, at the lateral dorsal axillary line. After tumor injection, the mice were turned to left decubitus position and observed for 45 to 60 min until fully recovered.

Luciferase-expressing cancer cells were imaged and quantified using IVIS200 system (Xenogen Corporation, Alameda, Calif.) at 10 minutes after i.p. injection of LUCW-ERIN™ (Caliper Life Sciences) before drug administration each time.

Pharmacokinetic and Biodistribution Studies

SCID mice bearing H460 lung cancer xenografts (~300 mm$^3$) were injected in the tail vein with either free drug doxorubicin (FD), liposomal doxorubicin (LD), or targeting (HSP1, HSP2 or HSP4) LD at a single dose of 2 mg/kg. At 1 hr and 24 hr post-injection, blood samples were collected through submaxillary punctures before mice were anaesthetized and sacrificed (three mice in each group). Then the mice were perfused with 50 ml PBS through heart, xenograft tumors and organs (brain, lung, heart, liver, and kidney) were dissected, weighted, and homogenized to calculate amount of doxorubicin in tissues. Total doxorubicin was quantified by measuring fluorescence at $\lambda_{Ex/Em}$=485/590 nm using a spectrofluorometer (SPECTRAMAX® M5, Molecular Devices).

Statistical Analysis

Two-sided unpaired Student's t-test was used to calculate P values. P<0.05 was considered significant for all analyses.

Results

Identification of Three Novel Peptides that Bind to Several Types of Human Lung Cancer Cells In this study, we used a phage-displayed random peptide library to isolate phages that were able to bind to H460 non-small cell lung carcinoma (NSCLC) cells. After five rounds of affinity selection (biopanning), the titer of bound phage increased by up to 9-fold. Ninety-four phage clones were randomly selected from both the fourth and the fifth rounds of biopanning for cellular ELISA screening. Forty-seven clones of these selected phages possessed higher affinity to H460 cells. We then further tested the binding activity of these H460 bound clones to other cell lines, including human lung adenocarcinoma H1993, CL1-5, A549, murine Lewis lung carcinoma 3LL or human normal nasal mucosal epithelial NNM cells. By sequencing phage clones with the highest lung cancer binding but the faintest normal cell reactivity, we identified thirteen phage clones, which displayed two distinctive groups of consensus sequences (Table 1). Its interesting that HPC1, 5 and 13 displayed identical sequence "GAMHLP-WHMGTL" (SEQ ID NO: 1). Table 1 shows alignment of phage-displayed peptide sequences selected by H460 cells. From 47 random selected phage clones in the fifth round of biopanning, 13 phage clones with higher H460 binding affinity were identified and the displayed-peptide sequences were aligned. *Phage-displayed consensus amino acids are shown in the box.

further study since they typified MHL-W motif, NPW-E motif, and W-EMM motifs, respectively.

To determine whether the peptide sequences displayed on HPC1, HPC2 and HPC4 have lung cancer binding function, we synthesized HSP1, HSP2, and HSP4 peptides, which have the amino acid sequences GAMHLPWHMGTL (SEQ ID NO: 1), NPWEEQGYRYSM (SEQ ID NO: 2) and NNP-WREMMYIEI (SEQ ID NO: 3), respectively. The words "SP" in "HSP" represented the "Synthetic Peptide" displayed by HPC phage. HSP1, HSP2 or HSP4 synthetic peptides or their fluorescein isothiocyanate (FITC) conjugates would be used in the following experiments. To verify whether HSP1, 2, and 4 peptides would bind to target molecules expressed on the surface of lung cancer cells, the surface binding activities of each FITC-conjugated peptides was analyzed by flow cytometry and immunofluorescent staining (FIG. 1A). In the FACS data, all of these three FITC-labeled peptides exhibited prominent binding to several pathological subtypes of human lung cancer cell lines, including large cell carcinoma (H460 and H661), adenocarcinoma (H1993, H441, CL1-5 and A549), squamous cell carcinoma (H520) and small cell carcinoma (H1688), but not to human normal bronchial epithelial cell (NL20). Furthermore, HSP1, 2, and 4 show different binding patterns of fluorescence intensity in various lung cancer cells, suggesting that these peptides might target different molecules on the cell surface.

In cell IFA experiments (FIG. 1A), FITC-labeled HSP1, 2 or 4 can bind to a major group of H460 large cell carcinoma cells and H1993 adenocarcinoma cells while FITC-labeled control peptide cannot. The FITC-positive cells represent the peptide target molecules expressing cells. Thus, we calculated the percentages of positively stained H460 and H1993

TABLE 1

| Phage clone | SEQ ID NO: | Phage-displayed peptide sequence* | Frequency |
|---|---|---|---|
| HPC1, 5, 13 | 1 | G A M H L P W H M G T L | 3/13 |
| HPC12 | 4 | G A M H L S W H M G T H | 1/13 |
| HPC10 | 5 | D P M H N N W H S S P I | 1/13 |
| HPC9 | 6 | G L D H L W W S S Q T P | 1/13 |
| HPC2 | 2 | N P W E E Q G Y R Y S M | 1/13 |
| HPC3 | 7 | N P W N E M W F Q T S R | 1/13 |
| HPC4 | 3 | N N P W R E M M Y I E I | 1/13 |
| HPC6 | 8 | W A D M M T S V T P W L | 1/13 |
| HPC7 | 9 | S E F P R S W D M E T N | 1/13 |
| HPC8 | 10 | Q H Y E T L A F R P K H | 1/13 |
| HPC11 | 11 | A T Y N S V N R H S A V | 1/13 |

To investigate whether these similar peptide-displayed phages exhibited similar binding, patterns to different lung cancers, we compared the binding intensity of these two groups of phages to H460, H1993, CL1-5, A549 and 3LL by cellular ELSA (Manuscript submitted for publication, which is incorporated hereby by reference in its entirety). The data revealed that although HPC2, 3 and 4 displayed similar sequences containing NPW-E (SEQ ID NO: 14) motif, HPC 3, 4 and 6 exhibited more similar binding patterns in various lung cancers. This suggested that W-EMM (SEQ ID NO: 15) mimetic motifs may play more important role than NPW-E motif in binding to lung cancers, since HPC3 and 4 consist both of these two motifs but behaved as HPC6, which contains only W-EMM mimetic motif. The other group of phages all displayed MHL-W (SEQ ID NO: 16) consensus sequence with similar binding patterns to lung cancers. Based on these findings, we chose to focus on HPC1, HPC2 and HPC4 for cells by these three peptides (FIG. 1B). Based on the statistic table and fluorescence pictures, we found out the proportions of target-expressing cells relative to the entire populations and the receptor densities on cell surface. It is worth noting that HSP4 showed higher receptor density on the cell surface as indicated by its stronger fluorescent intensity despite having lower positive rate in H1993 cells. In addition, HSP4 peptides showed the best reactivity to H460 cells, both in terms of percentage of positive cells and receptor density. These results suggest that HSP1, 2, and 4 are able to bind to both NSCLC and SCLC cells in vitro with different binding patterns.

In Vivo Tumor Homing and Imaging of HPC1, 2, and 4

To investigate the targeting ability of the selected phage clones in vivo, we intravenously injected each clone into mice bearing H460-derived tumor xenografts. After perfusion, we measured the phage titers in the tumor and normal organs.

The tumor homing ability was estimated by the phage titer ratio of tumor to normal organs, comparing to control phage. In the first group of phages with consensus sequence (HPC2, 3, 4, 6), HPC2, 3 and 4 showed prominent tumor homing ability, whereas HPC6 exhibited only recessive tumor localization iii vivo (FIG. 2A). That was another reason why we chose HPC2 and HPC4, but not HPC6, to typify NPW motif and W-EMM motif for further study. In the other group of phages with consensus sequence of MHL-W, HPC1, but not HPC9, exhibited notable tumor homing ability (FIG. 2A).

Figure 2C:
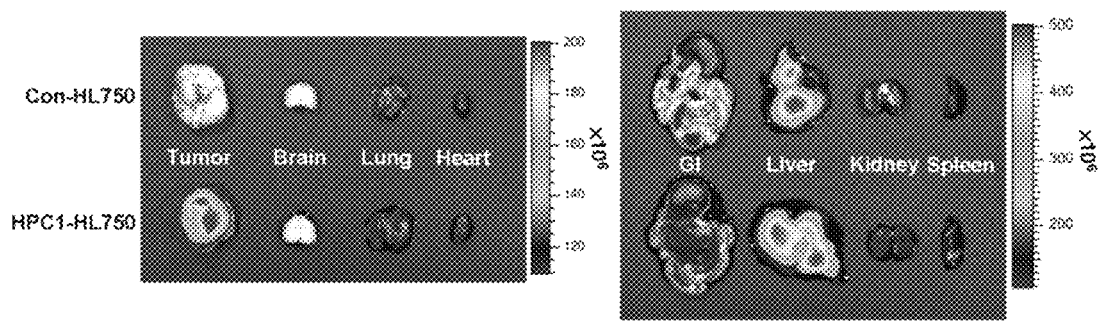

Further, we labeled phages with HILYTE™ Fluor 750 (HL750) fluorescence dye, which can be used for whole body imaging at specific ranges of excitation and emission wavelength (Excitation: 710/760 nm; Emission: 810/875 nm). SCID mice beating size-matched H460 xenografts were i.v. injected with HPC1-HL750, HPC2-HL750, HPC4-HL750 or control phage-HL750 and serially monitored by IVIS200. The HL750-labeled phages were visible under IVIS200 imaging system while systemic circulating through the mice. After 6 hr post-injection, the targeting phages, which accumulated in tumor tissue, became obvious and could be easily seen. At 24 hr post-injection, fluorescence imaging of mice and the dissected tissues were captured (FIG. 2C). The tumor fluorescent intensities in the targeting phage groups were about 3 to 4-fold higher than that in the control phage group (FIG. 2B). These results indicate that all of HPC1, HPC2 and HPC4 possess significant tumor-homing ability.

Figure 3B:
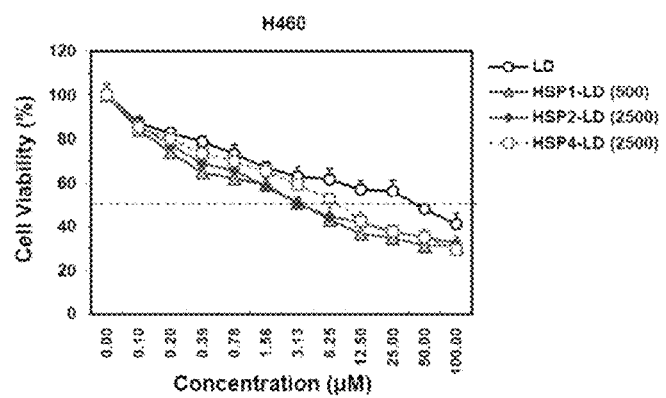
FIGS. 3A-B show HSP1, HSP2 and HSP4 peptides enhanced liposomal SRB internalization and liposomal doxorubicin cytotoxicity in human lung cancer cell line H460. (A) Kinetics of HSP1-LSRB, HSP2-LSRB, HSP4-LSRB and LSRB uptake by H460 cells with incubation at 37° C. After acid glycine buffer washing, which removed surface-bound liposomal dye, the internalized SRB was quantified (n=4) (B) H460 cells were treated with increasing amounts of targeting or non-targeting liposomal doxorubicin (LD), then analyzed cell viability by MTT assay (n=6). The $IC_{50}$ of HSP1-LD, HSP2-LD, HSP4-LD and LD are 3.512 µM, 3.388 µM, 4.646 µM and 43.865 µM respectively. The suitable peptide numbers for HSP1, 2 and 4 inserted per liposome were tested.
Figure 3A:
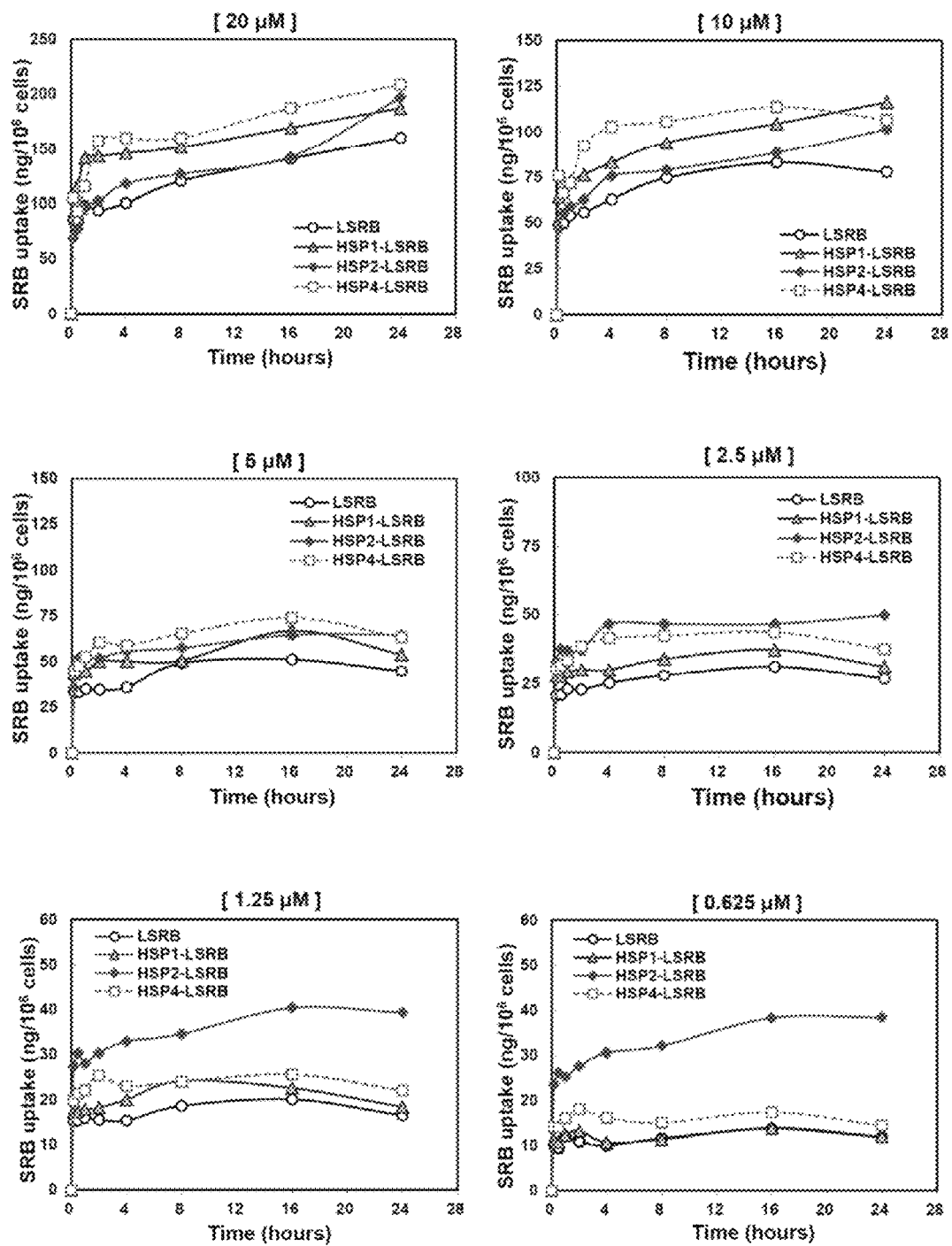

HSP1, 2 and 4 Synthetic Peptides Improved Liposomal Drug Binding, Intracellular Delivery and Cytotoxicity Since "receptor-mediated endocytosis" is crucial for targeting drug delivery due to improved drug penetration, release and efficacy, we next examined whether HSP1, HSP2 or HSP4 could promote liposomal drug internalization to human lung cancer cells. For materials preparation HSP1, HIS2 and HSP4 were conjugated to NHS-PEG-DSPE before inserted to the external surface of liposomal nanoparticles by phospholipid DSPE. These nanoparticles contained sulforhodamine B (SRB; fluorescence reagent) or doxorubicin. Unlike chemotherapeutic drugs, fluorescence dye SRB wound not cause cell death even at high concentration, making it an ideal tool for measuring the uptake efficiency of living cells. In the time course experiment, we found targeting peptide (HSP1, 2 or 4)—conjugated liposomal SRB (LSRB) enhanced liposome internalization in H460 (FIG. 3A) and H1993 cells compared to non-targeting LSRB. Interestingly, we also observed that HSP2 exhibited prominent intracellular delivery at low LSRB concentrations, while no difference from non-targeting LSRB at high concentration in H460 cells was observed (FIG. 3A). On the contrary. HSP1 and HSP4 showed better uptake ability at higher doses. One possible explanation for this phenomenon is that the receptors of HSP2 on H460 cell surface were saturated at high concentration. This phenomenon suggests that HSP1, 2, or 4 may target different receptors on the cell surface due to the different receptor densities.

For visual imaging, we also examined the targeting peptide-conjugated LSRB in lung cancer cells using confocal microscopy. We observed a large amount of LSRB in the cytoplasm of H460 cells incubated with HSP1-LSRB, HSP2-LSRB or HSP4-LSRB at 37° C., whereas little SRB fluorescence was detectable in cells incubated with non-targeting LSRB. At 4° C., all of the LSRB conjugated these three targeting peptides bound to the outer membrane of the H460 cells. It is worth noting that HSP1 peptide exhibited stronger ability at binding than internalization, compared to HSP2 and HSP4, as evident by its stronger binding intensity at 4° C. but weaker SRB fluorescence in cytosol at 37° C.

Furthermore, we examined whether HSP1, 2, and 4-mediated liposomal drugs enhanced the therapeutic efficacy of drugs due to their proven targeting and endocytosis abilities. We performed in vitro cytotoxicity assays for HSP1, 2, or 4-conjugated liposomal doxorubicin (LD) in H460 cells (FIG. 3B). Compared to LD, all of these three targeting peptide-LD significantly enhanced the cytotoxicity of the drug to cancer cells. HSP1, HSP2 and HSP4, at its optimal peptide ratio, decreased the half maximal inhibitory concentration ($IC_{50}$) in H460 cells by 12.5-, 13- and 9.4-fold, respectively (FIG. 3B).

In brief, HSP1, 2 and 4 targeting peptides not only bind to lung cancer cell with high specificity, but they also trigger liposomal drug internalization and enhance therapeutic efficacy in vitro.

Figure 4A:
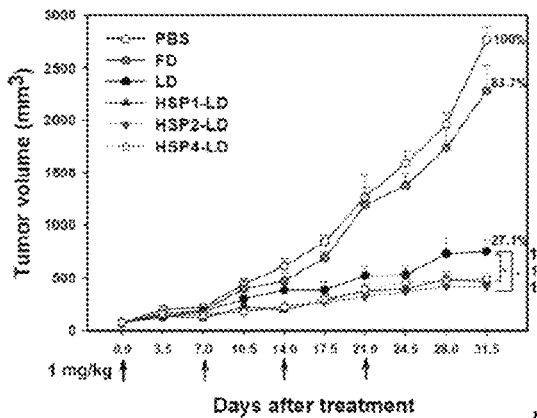
FIGS. 4A-F show therapeutic efficacy of HSP1-LD, HSP2-LD and HSP4-LD in human lung large cell carcinoma xenografts. (A) Mice bearing H460-derived lung cancer xenografts with average tumor size of ~75 mm³ were administered with FD, LD, HSP1-LD, HSP2-LD, HSP4-LD (1 mg/kg/injection once a week), or an equal volume of PBS intravenously. n=8 in each group. Points, mean tumor volumes. (B) Mice bearing size-matched H460-derived lung cancer with tumor size of ~500 mm³ were treated with FD, LD, HSP1-LD, HSP2-LD, HSP4-LD (2 mg/kg/injection, twice a week), or an equal volume of PBS by intravenous injection. n=7 in each group. The detailed statistic information of HSP1-LD HSP2-LD and HSP4-LD efficacy are separately shown in (C-E). Error bar, SE. *, $P<0.05$ , $P<0.01$; *, $P<0.001$. (F) A Kaplan-Meier survival plot showed longer lifespan of targeting drugs than non-targeting drugs in large tumor treatment.
Figure 4B:
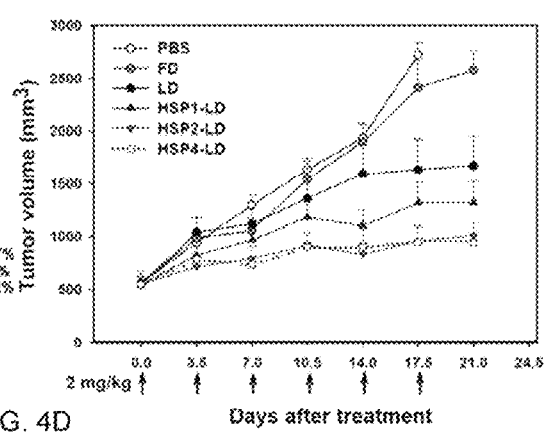
Figure 4C:
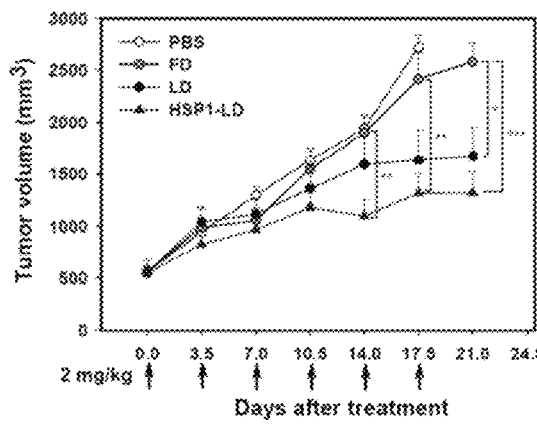
Figure 4D:
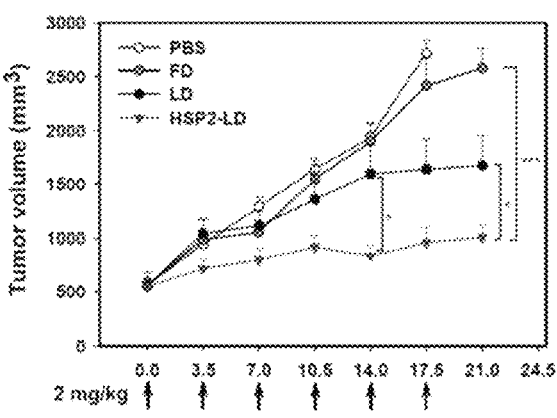
Figure 4E:
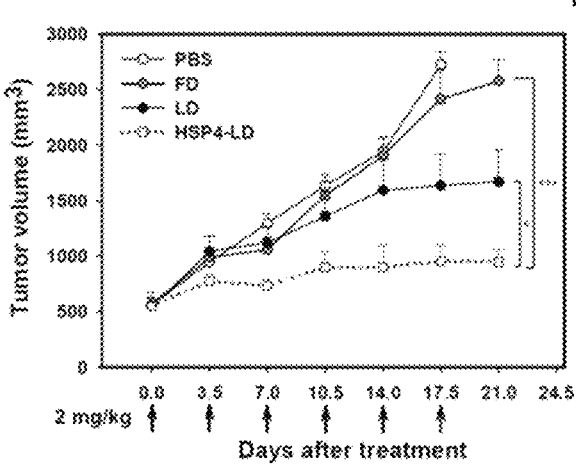
Figure 4F:
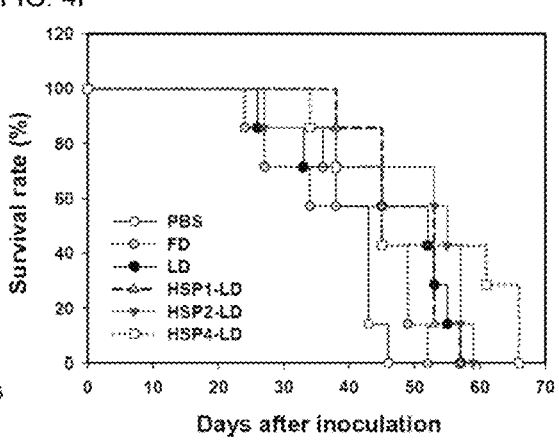

Therapeutic Efficacy of HSP1, HSP2 and HSP4-Mediated Drug Delivery Systems in Human Large Cell Carcinoma and Adenocarcinoma Xenograft Models Further, to determine whether HSP1, 2 and 4 could improve the chemotherapeutic efficacy of anticancer drugs in vivo, we formulated targeting drug delivery systems by coupling these peptides with PEGylated liposomal doxorubicin (LD). In the first experiment, SCID mice bearing H460 human lung large cell carcinoma xenografts were administered intravenously with HSP1-LD, HSP2-LD, HSP4-LD, non-targeting LD, free doxorubicin (FD) or equivalent volumes of PBS (FIGS. 4A-F). We examined the therapeutic efficacies of these targeted-LDs in both small tumor (average tumor size of ~75 $min^3$) (FIG. 4A) and large tumor (average tumor size of 500 $mm^3$) (FIGS. 4B-D), respectively. Anticancer efficacy was evaluated by determining the average tumor volumes while the side-effects were estimated by measuring body weight changes throughout the period of treatment. The mice bearing small tumor were treated with 1 mg/kg of doxorubicin once a week for 4 times. The tumor volume decreased significantly in targeting-LD groups (FIG. 4A). In the mice beating large tumor treatment, the targeting peptides HSP1, 2, and 4 significantly improved therapeutic efficacy of LD in H460 large tumor, especially HSP2 and HSP4-LD, which showed a decrease in tumor volume by half compared to the LD group (FIGS. 4B-E). The result of in vivo biodistribution and pharmacodynamics study could support this finding that HSP2 and HSP4 exhibited better drug delivery efficacy of LD to H460 tumor tissues. The prolonged overall survival rates were observed (FIG. 4F) and body weight had not changed significantly during the course of treatment.

Figure 5A:
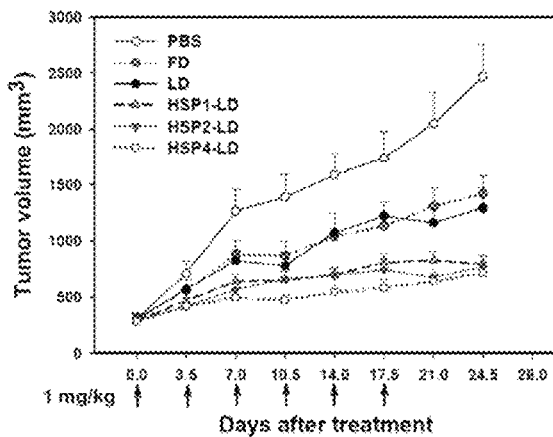
FIGS. 5A-F show therapeutic efficacy of HSP1-LD, HSP2-LD and HSP4-LD in human lung adenocarcinoma xenografts. (A) Mice bearing H1993-derived lung cancer xenografts with average tumor size of ~300 mm³ were administered with FD, LD, HSP1-LD, HSP2-LD, HSP4-LD (1 mg/kg/injection, twice a week), or an equal volume of PBS intravenously. n=7 in each group. Points, mean tumor volumes. The detailed statistic information of HSP1-LD, HSP2-LD and HSP4-LD efficacy are separately shown in (B-D) Error bar, SE. *, $P<0.05$; , $P<0.01$; *, $P<0.001$. (E) Both Weight change during the course of treatment. NS, no significance. (F) A Kaplan-Meier survival curve showed markedly longer lifespan of mice treated with HSP1 and HSP2-mediated liposomal drug than other groups in H1993 model.
Figure 5B:
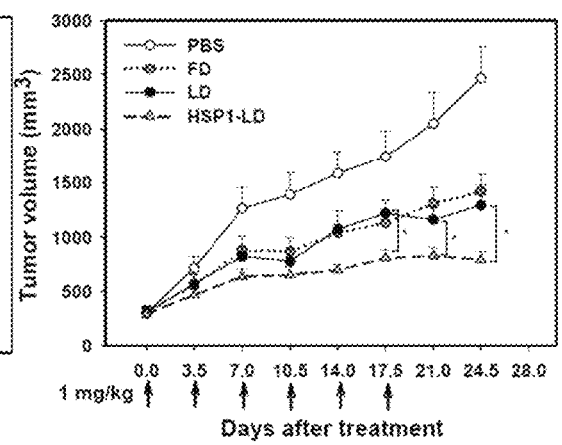
Figure 5C:
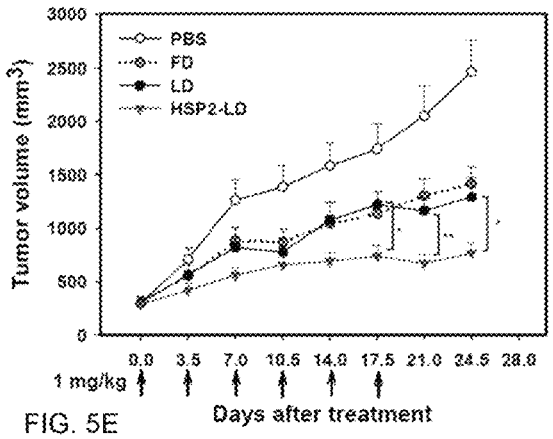
Figure 5D:
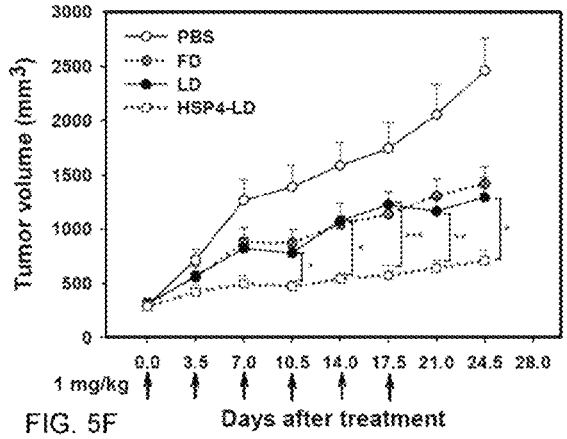
Figure 5E:
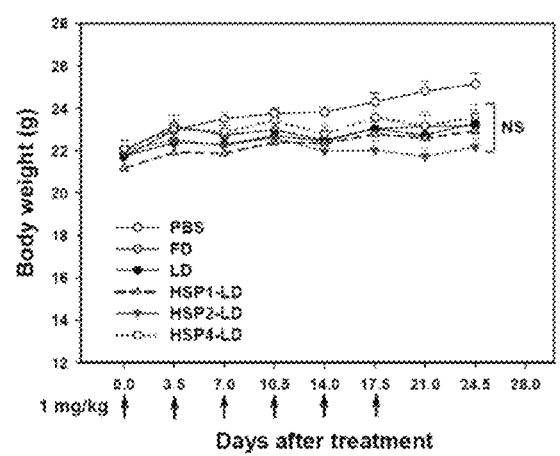
Figure 5F:
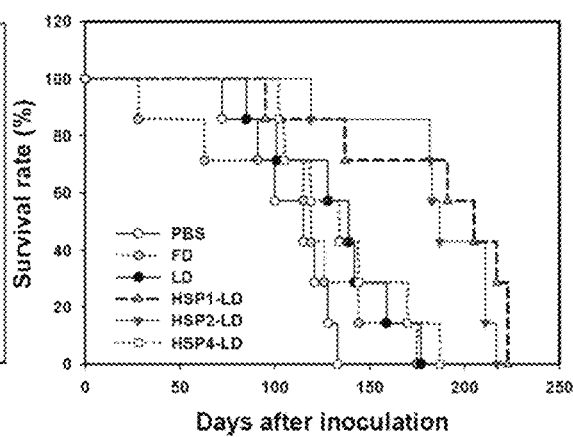

We also examined the therapeutic effect of HSP1, 2, and 4-LD in H1993 human lung adenocarcinoma xenograft model (FIGS. 5A-F). Mice hearing size matching H1993 large tumor were injected intravenously with 1 mg/kg of HSP1-LD, HSP2-LD, HSP4-LD, LD, FD or equivalent volumes of PBS twice a week for three weeks. FIG. 5E showed that administration of HSP1, 2, and 4-LD did not cause an appreciable reduction in body weight as compared to the LD group, HSP4-LD showed the best therapeutic effect, as measured by tumor volume since the tumor size was significantly decreased as early as 10.5 days after treatment (after 3 injections) (FIGS. 5B-D). However, in terms of overall survival rate, mice treated with HSP1 and HSP2-LD lived 50-60 days longer than that treated with LD (FIG. 5F). These data indicate that decrease in tumor volumes does not translate into prolonger overall survival rates. One of the possible explanations for this was that although HSP4 had the highest receptor number on H1993 cell surface (FIG. 1A) compared to the other two peptides, there were only 55.93% of H1993 cells expressing the receptor of HSP4, which was less than that of HSP1 and 2 (FIG. 1B). This might provide more chances for those HSP4-negative cells, which would be selected to become drug-resistant cells during HSP4-LD treatment in H1993 model.

HSP1, 2 and 4 Targeting Peptides Enhanced Minor Drug Delivery In Vivo by Biodistribution Assay To explore the mechanisms underlying the enhanced anticancer effects of HSP1, 2, or 4-conjugated liposomal drugs in vivo, we performed a pharmacodynamics and biodistribution study to measure the drug accumulation in tumor tissues. Mice bearing H460 xenograft tumor were intravenously injected with a single dose of 2 mg/kg FD, LD, HSP1-LD, HSP2-LD or HSP4-LD. After 1 hr and 24 hr systemic circulation, the doxorubicin concentration in serum, tumors and normal organs were estimated by measuring fluorescence signal of doxorubicin after purification steps. The mean intra-tumor doxorubicin concentrations in the HSP1, HSP2, and HSP4-LD groups were about 1.5-, 2- and 2-fold higher than that in the LD group, respectively. This data provided evidence and explanation for the superior tumor inhibitory effects exhibited by HSP2 and 4 in the previous experiment comparing H460 large tumor treatment using targeting-LD (FIGS. 4B-F). Since doxorubicin worked by intercalating DNA, the drugs accumulated in cancer nuclei were also measured. The results generally paralleled those in the tumor. Liposomal formulation drugs (LD, HSP1-LD, HSP2-LD, and HSP4-LD) displayed similar biodistribution profiles in plasma and normal organs, whereas free form of doxorubicin exhibited much shorter half-life in plasma. The results from this experiment demonstrated that HSP1, 2, and 4 elevated the penetration of anticancer drugs into tumor and resulted in higher accumulation of the drugs at their intracellular target sites, thereby enhancing the therapeutic efficacy of doxorubicin. In addition, these targeting peptides did not increase doxorubicin accumulated in normal organs such as brain, heart, lungs, liver and kidney in animal models.

Targeting Liposome-Based Combination Therapy Further Improved Overall Survival

Figure 6A:
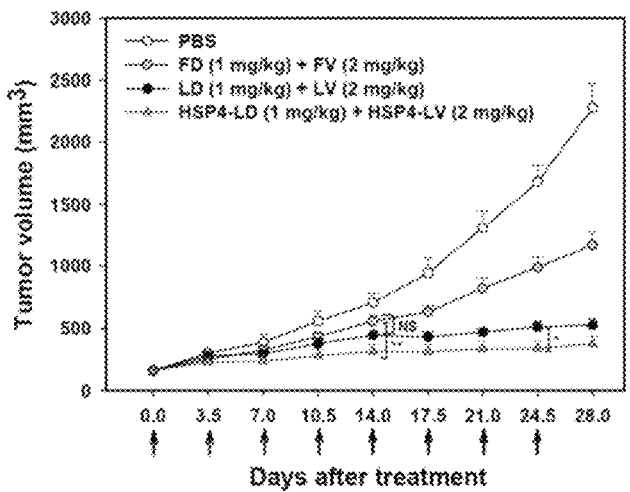
FIGS. 6A-D show combination therapy of HSP4-LD and HSP4-LV in human lung large cell carcinoma xenografts. (A) Mice bearing H460-derived lung cancer xenografts with average tumor size of ~200 mm³ were administered with FD/FV, LD/LV or HSP4-LD/HSP4-LV at combination doses of ½ mpk, respectively, twice a week for four weeks, or an equal volume of PBS intravenously. n=8 in each group. Points, mean tumor volumes. Error bar, SE, *, $P<0.05$; **, $P<0.01$ (B) Body weight change during the course of treatment NS, no significance. (C) A Kaplan-Meier survival curve showed markedly longer lifespan of mice treated with HSP4 mediated liposomal drugs than other groups in H460 model. (D) Median survival days were significantly prolonged by HSP4 targeting LD and LV.
Figure 6B:
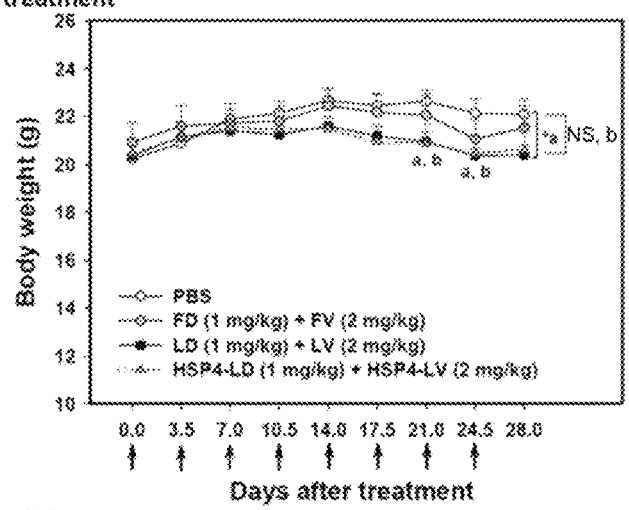
Figure 6C:
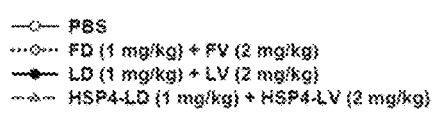
Figure 6D:
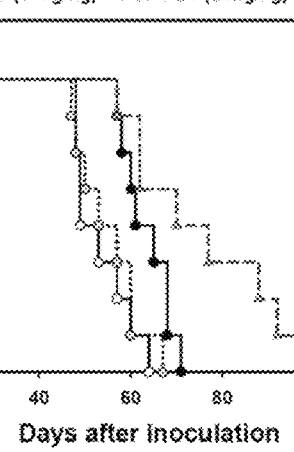

Given the genomic instability and genetic heterogeneity of cancer biology, single-drug monotherapy often strengthens the redundant signaling pathways, accelerating chemoresistant mutations and recurrence. The use of multiple chemotherapeutics with different mechanisms of actions in combination has become the primary strategy to treat drug, resistant cancers. Therefore, we co-delivered HSP4-LD and HSP4-conjugated liposomal vinorelbine (LV), which acts as a microtubule inhibitor at a 1:2 combinatorial ratio, to treat H460 xenograft model (FIGS. 6A-D). The administration regimen of these two drugs had been tested and optimized by therapeutic synergism in vivo (data not shown). FIGS. 6C-D showed that HSP4-mediated combinatorial targeting liposome-treated group had a much longer overall survival than non-targeting liposome- or free drug-treated groups. The combinatorial targeting liposome-treated group prolonged median survival compared to non-targeting liposome-treated group by up to 11 days (74 vs. 63 days).

We also investigated this 1:2 LD and LV combinatorial regimen in H460 large cell carcinoma FIGS. 7A-E) and A549 adenocarcinoma (FIGS. 8A-E) orthotopic models, which successfully recapitulated tumor-microenvironment interactions. In H460 orthotopic model, luciferase-expressing tumor mass decreased significantly in HSP4-mediated combinatorial liposome-treated group (FIGS. 7A-B) compared to free drug-treated group, while non-targeting liposome-treated group showed no significant differences to free drugs group. Since H460 orthotopic model was highly aggressive, all mice underwent severe body weight loss due to cancer cachexia syndrome (FIG. 7C). However, the prolonged median survival time was observed by 6.5 days in targeting liposome group compared to nontargeting liposome group (77.5 vs. 71 days). In terms of A549 orthotopic model, HSP4-mediated combinatorial liposome-treated group significantly prolonged overall survival rate and increased median survival times by up to 47 days compared to non-targeting liposome-treated group (131 vs 84 days) (FIGS. 8D-E). We can demonstrate that HSP4 targeting peptide not, only improved the therapeutic efficacy of nanodrugs (FIGS. 8A-B), but also reduced adverse effect by decreasing body weight loss (FIG. 8C).

Figure 9:
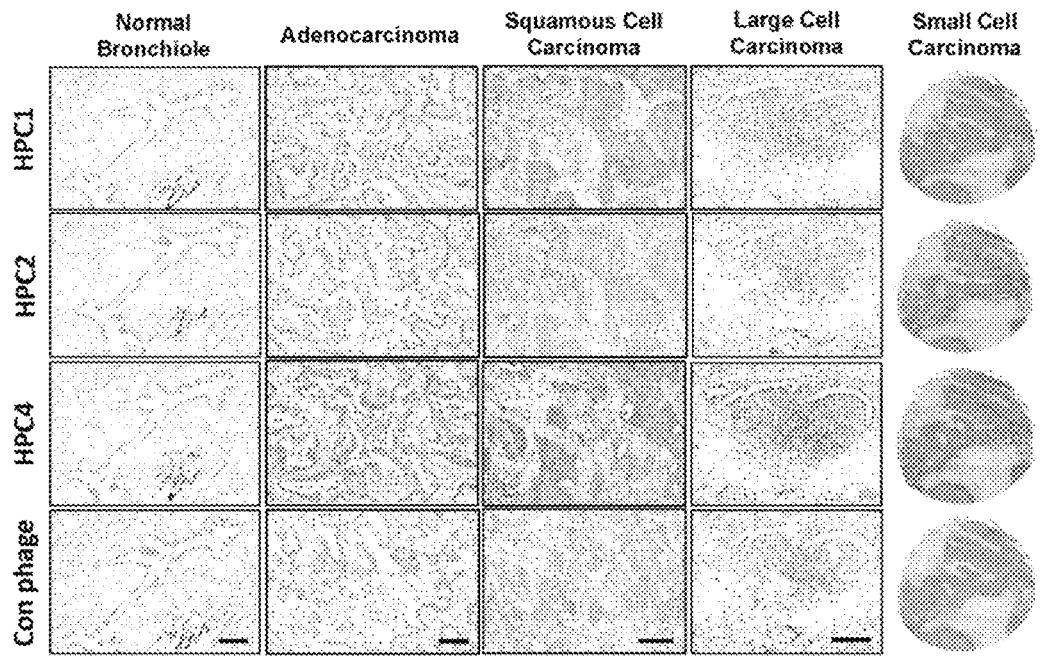
FIG. 9 shows IHC staining of HPC1, 2 and 4 to NSCLC and SCLC clinical specimens. Representative photomicrographs of paraffin sections from several types of human lung cancer surgical specimens were detected using HPC1, HPC2, and HPC4 phage clones ($2 \sim 5 \times 10^8$ pfu/µl). In comparison, normal bronchiole was not detected by these targeting phages. Helper phage was used as negative control. Scale bar, 100 µm.

Binding Activities of HPC1, 2, and 4 to Clinical Surgical Specimens of Human Lung Cancer The response rate of a targeting drug to biopsies or surgical specimens of cancer patients is one of the most difficult challenges facing clinical drug development. Here, we examined whether HSP1, 2 or 4 would react to several different types of human lung cancer specimens, including adenocarcinoma. papillary adenocarcinoma, bronchioloalveolar carcinoma (BAC), squamous cell carcinoma (SCC), large cell carcinoma, and small cell carcinoma. Since M13 phage particles consisted of many coat proteins, the signals were amplified under immunostaining steps and were more visible than using peptides themselves. For this reason, we used HPC1, 2, and 4 phages for human tissue staining. Table 2A lists the percentages of the positive rates of HPC1, 2, and 4 for cancer detections in several different types of lung cancers. In general, HPC4 displayed the best reactivity (>80%) in almost all types of lung cancers, which was followed by HPC1 (>50%). Moreover, HPC1, 2 and 4 also recognized metastatic adenocarcinoma or SCC from lung (Table 2B), but exhibited no reaction for normal lung tissue or cancer adjacent normal lung tissue (Table 2C). FIG. 9 shows examples of immunohistochemistry staining obtained on consecutive sections from individual tumors. These data demonstrate that HPC1, 2, and 4 can recognize not only NSCLC but also SCLC surgical specimens, but do not cross-react to normal pneumonic tissues Tables 2A-C show detection of human lung cancer surgical specimens by HPC1, 2 and 4 using immunohistochemistry. Several histopathological subtypes of clinical human lung cancer biopsies were immunostained by HPC1, 2 or 4 and compared to control phage (Table 2A). The positive response percentages were calculated and compiled IHC data of metastatic adenocarcinoma and SCC from lung (Table 2B). Normal pneumonic tissue and cancer adjacent normal pneumonic tissue were confirmed for HPC1, HPC2 and HPC4 tumor specificity (Table 2C). Reaction area: +++, >50%; ++, 50~20%; +, <20%; −, 0%.

TABLE 2A

| | Total case no. | +++ | ++ | + | − | % Positive |
|---|---|---|---|---|---|---|
| Adenocarcinoma | | | | | | |
| HPC1 | 27 | 0 | 6 | 13 | 8 | 70.37 |
| HPC2 | | 1 | 2 | 9 | 15 | 44.44 |
| HPC4 | | 5 | 18 | 2 | 2 | 92.59 |
| Con phage | | 0 | 0 | 0 | 27 | 0.00 |
| Papillary adenocarcinoma | | | | | | |
| HPC1 | 8 | 2 | 1 | 3 | 2 | 75.00 |
| HPC2 | | 0 | 1 | 3 | 4 | 50.00 |
| HPC4 | | 1 | 5 | 1 | 1 | 87.50 |
| Con phage | | 0 | 0 | 0 | 8 | 0.00 |
| Bronchioaveolar carcinoma | | | | | | |
| HPC1 | 8 | 2 | 4 | 1 | 1 | 87.5 |
| HPC2 | | 0 | 0 | 1 | 7 | 12.5 |
| HPC4 | | 1 | 5 | 1 | 1 | 87.5 |
| Con phage | | 0 | 0 | 0 | 8 | 0 |

TABLE 2A-continued

| | Total case no. | +++ | ++ | + | − | % Positive |
|---|---|---|---|---|---|---|
| Squamous cell carcinoma | | | | | | |
| HPC1 | 27 | 5 | 7 | 12 | 3 | 88.89 |
| HPC2 | | 0 | 2 | 7 | 18 | 33.33 |
| HPC4 | | 9 | 16 | 1 | 1 | 96.30 |
| Con phage | | 0 | 0 | 0 | 27 | 0.00 |
| Large cell carcinoma | | | | | | |
| HPC1 | 10 | 0 | 6 | 3 | 1 | 90.00 |
| HPC2 | | 0 | 0 | 4 | 6 | 40.00 |
| HPC4 | | 5 | 4 | 0 | 1 | 90.00 |
| Con phage | | 0 | 0 | 0 | 10 | 0.00 |
| Small cell carcinoma | | | | | | |
| HPC1 | 8 | 2 | 5 | 1 | 0 | 100 |
| HPC2 | | 0 | 0 | 2 | 6 | 25.00 |
| HPC4 | | 5 | 3 | 0 | 0 | 100 |
| Con phage | | 0 | 0 | 0 | 8 | 0.00 |

TABLE 2B

| | Total case no. | +++ | ++ | + | − | % Positive |
|---|---|---|---|---|---|---|
| Metastatic adenocarcimoma from lung | | | | | | |
| HPC1 | 8 | 0 | 1 | 6 | 1 | 87.50 |
| HPC2 | | 0 | 0 | 3 | 5 | 37.50 |
| HPC4 | | 2 | 4 | 2 | 0 | 100 |
| Con phage | | 0 | 0 | 0 | 8 | 0.00 |
| Metastatic squamous cell carcinoma from lung | | | | | | |
| HPC1 | 4 | 0 | 2 | 0 | 2 | 50.00 |
| HPC2 | | 0 | 0 | 1 | 3 | 25.00 |
| HPC4 | | 2 | 2 | 0 | 0 | 100 |
| Con phage | | 0 | 0 | 0 | 4 | 0.00 |

TABLE 2C

| | Total case no. | +++ | ++ | + | − | % Positive |
|---|---|---|---|---|---|---|
| Metastatic adenocarcimoma from lung | | | | | | |
| HPC1 | 6 | 0 | 0 | 0 | 6 | 0.00 |
| HPC2 | | 0 | 0 | 0 | 6 | 0.00 |
| HPC4 | | 0 | 0 | 0 | 6 | 0.00 |
| Con phage | | 0 | 0 | 0 | 6 | 0.00 |
| Metastatic squamous cell carcinoma from lung | | | | | | |
| HPC1 | 6 | 0 | 0 | 0 | 6 | 0.00 |
| HPC2 | | 0 | 0 | 0 | 6 | 0.00 |
| HPC4 | | 0 | 0 | 0 | 6 | 0.00 |
| Con phage | | 0 | 0 | 0 | 6 | 0.00 |

In contrast to monoclonal antibodies, which exhibit large size, poor tumor penetration, and high immunogenicity when used as targeting ligands (Cheng and Allen, 2010), peptide ligands are the better choice for payload delivery because of smaller size, less immunogenicity, higher tumor penetration, more cost-effective for synthesis and production. In this study, we identified three novel peptides HSP1, 2 and 4 that could selectively bind to several types of human lung cancer, but not normal pneumonic tissue in vitro, in vivo, and among clinical samples. Thirteen phage clones (HPC1-13) with higher lung cancer binding in vitro were divided into two major categories by distinct consensus sequences, in which the first group displayed "MHL-W" motif (HPC1) while the other displayed "NPW-E or W-EMM" motif (HPC2 and 4). Although HPC2 and 4 displayed more similar sequences, they showed different binding patterns and distinct functional behaviors in serial experiments, such as cellular ELISA binding assay, FACS analysis, cell IFA staining (FIGS. 1A-B), dose-dependent and time course LSRB uptake assay (FIG. 3A), and even human surgical specimens detection (FIG. 9; Table 2). These findings imply that HSP1, 2, and 4 may target different protein molecules on the cell surface of lung cancers due to their different positive-stained rates, reactive intensities, or receptor densities.

HSP1, 2, and 4-mediated DDS can specifically bind to lung cancer cells, which in turn trigger "receptor-mediated endocytosis" to discharge payloads to their intracellular target site (for example, DNA for doxorubicin), resulting in about 10-fold reduction in $IC_{50}$ in vitro (FIGS. 3A-B). Likewise, HSP1, 2, and 4-mediated liposomal drugs significantly improved drug bioavailability in vivo, leading to increased therapeutic index (FIGS. 4-8). It should be noted that HSP2 and 4 performed better in LD delivery by increasing both tumor accumulation and therapeutic efficacy (FIGS. 4B-C) by up to 2-fold in H460 xenograft model. Unlike its consensus sequence-displayed member HSP2, HPC4, which positively stained nearly all types of NSCLC and SCLC surgical specimens, exhibited the best clinical reactivity (Table 2). In addition, preclinical data also highlight the advances of HSP4-mediated combinatorial liposomes in overall survival (FIGS. 6-8), this strategy promises a novel and better tailored combinatorial regimen to overcome clinical chemoresistance and delay cancer relapse.

IHC data (FIG. 9; Table 2) also revealed that W-EMM motif of HSP4 might contribute more significantly to this effect than NPW-E motif, thus was vital for clinical application. More advanced studies are needed to investigate the detailed functions of each motif in order to choose the appropriate motifs for endocytosis and for other clinical detections. Hence, we can modify the peptide sequences into perfection and multi-functions.

Further research would be necessary to elucidate the receptor proteins expressed on lung cancer cell surface targeted by HSP1, HSP2 and HSP4 and to investigate their respective downstream intracellular signals critical to the transport of the cargos released. Target protein identification will also provide information on safety and toxicity profiles, which are crucial for the development of targeting drugs for clinical use. Based on our research, HSP1, 2 and 4 lung cancer targeting peptides bear significant potential to be developed into "theranostics nanoparticles" with broad clinical applications including targeting therapy, companion diagnostics and non-invasive imaging.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. A conjugate comprising:
   (a) an isolated or a synthetic targeting peptide of less than 15 amino acid residues in length, comprising an amino acid sequence having at least 90% identity to a sequence selected from the group consisting of SEQ ID NOs: 2-8; and
   (b) a component conjugated to the targeting peptide, the component being selected from the group consisting of a drug delivery vehicle, an anti-cancer drug, a micelle, a nanoparticle, a liposome, a polymer, a lipid, an oligonucleotide, a peptide, a polypeptide, a protein, a cell, an imaging agent, and a labeling agent.

2. An isolated or a synthetic targeting peptide of less than 15 amino acid residues in length, comprising an amino acid sequence having at least 90% identity to a sequence selected from the group consisting of SEQ ID NOs: 2-8, wherein the isolated or the synthetic targeting peptide is active in binding to a human lung cancer cell, but not to a normal cell.

3. The isolated or a synthetic targeting peptide of claim 2, which is conjugated to a component selected from the group consisting of a drug, delivery vehicle, a liposome, a polymer, a lipid, a cell, an imaging agent, and a labeling agent.

4. The isolated or a synthetic targeting peptide of claim 2, which is conjugated to a PEG-phospholipid derivative, a liposome, or a PEGylated liposome.

5. The isolated or a synthetic targeting peptide of claim 4, wherein the PEG-phospholipid derivative is selected from the group consisting of NHS-PEG-DSPE, PEG-DSPE.

6. The isolated or a synthetic targeting peptide of claim 4, further comprising an anti-cancer drug or a fluorescent dye encapsulated within the liposome, or the PEGylated liposome.

7. A composition comprising:
 (a) liposomes or PEGylated liposomes; and
 (b) at least one isolated or one synthetic targeting peptide of claim 2, conjugated to the surfaces of the liposomes or the PEGylated liposomes.

8. The composition of claim 7, comprising at least two isolated or synthetic targeting peptides conjugated to the surfaces of the liposomes or PEGylated liposomes.

9. The composition of claim 7, wherein each of the liposomes or PEGylated liposomes has a different targeting peptide conjugated thereto.

10. The composition of claim 7, further comprising at least one anti-cancer drug encapsulated within the liposomes or PEGylated liposomes.

11. The composition of claim 1, wherein the imaging agent is iron oxide.

12. The composition of claim 11, wherein the iron oxide is a nanoparticle.

13. The composition of claim 1, wherein the targeting peptide comprises at least one motif selected from the group consisting of MHLXW (SEQ ID NO: 16), NPWXE (SEQ ID NO: 14), and WXEMM (SEQ ID NO: 15) motifs, where X is any amino acid residue.

14. The isolated or a synthetic targeting peptide of claim 2, which contains one substitution modification relative to the sequence selected from the group consisting of SEQ ID NO: 2-8.

15. A method of treating lung cancer, comprising:
 administering to a subject in need thereof the composition of claim 10.

16. A method of detecting lung cancer cells, comprising the steps of:
 (1) exposing the cancer cells to a conjugate comprising:
  (a) at least one isolated or synthetic targeting peptide of claim 2; and
  (b) an imaging agent or a labeling agent, conjugated to the isolated or synthetic targeting peptide; and
 (2) removing the conjugate unbound to the cancer cells and detecting the imaging agent or the labeling agent conjugated to the isolated or a synthetic targeting peptide bound to the cancer cells; or
 (i) exposing the cancer cells to a conjugate comprising:
  (a') at least one isolated or synthetic targeting peptide of claim 2; and
  (b') at least one phage, the surface of which is conjugated to and displays the isolated or synthetic targeting peptide; and
 (ii) removing the conjugate unbound to the cancer calls and detecting the phage bound to the cancer cells.

17. The method of claim 16, wherein the cancer cells are present in a tissue specimen.

18. A conjugate comprising:
 (a) an isolated or a synthetic targeting peptide of less than 15 amino acid residues in length, comprising an amino acid sequence having at least 90% identity to the amino acid sequence of SEQ ID NO: 1; and
 (b) a component conjugated to the targeting peptide, the component being selected from the group consisting of a PEG-phospholipid derivative, a liposome, a PEGylated liposome, and an oligonucleotide.

19. The conjugate of claim 18, further comprising an anti-cancer drug or a fluorescent dye encapsulated within the liposome or the PEGylated liposome.

20. A method of treating lung cancer, comprising:
 administering to a subject in need thereof a conjugate of claim 18.

* * * * *

```
                              SEQUENCE LISTING

<160> NUMBER OF SEQ ID NOS: 16

<210> SEQ ID NO 1
<211> LENGTH: 12
<212> TYPE: PRT
<213> ORGANISM: Artificial Sequence
<220> FEATURE:
<223> OTHER INFORMATION: HSP1

<400> SEQUENCE: 1

Gly Ala Met His Leu Pro Trp His Met Gly Thr Leu
1               5                   10

<210> SEQ ID NO 2
<211> LENGTH: 12
<212> TYPE: PRT
<213> ORGANISM: Artificial Sequence
<220> FEATURE:
<223> OTHER INFORMATION: HSP2

<400> SEQUENCE: 2

Asn Pro Trp Glu Glu Gln Gly Tyr Arg Tyr Ser Met
1               5                   10

<210> SEQ ID NO 3
<211> LENGTH: 12
<212> TYPE: PRT
<213> ORGANISM: Artificial Sequence
<220> FEATURE:
<223> OTHER INFORMATION: HSP4

<400> SEQUENCE: 3

Asn Asn Pro Trp Arg Glu Met Met Tyr Ile Glu Ile
1               5                   10

<210> SEQ ID NO 4
<211> LENGTH: 12
<212> TYPE: PRT
<213> ORGANISM: Artificial Sequence
<220> FEATURE:
<223> OTHER INFORMATION: HPC12

<400> SEQUENCE: 4

Gly Ala Met His Leu Ser Trp His Met Gly Thr His
1               5                   10

<210> SEQ ID NO 5
<211> LENGTH: 12
<212> TYPE: PRT
<213> ORGANISM: Artificial Sequence
<220> FEATURE:
<223> OTHER INFORMATION: HPC10

<400> SEQUENCE: 5

Asp Pro Met His Asn Asn Trp His Ser Ser Pro Ile
1               5                   10

<210> SEQ ID NO 6
<211> LENGTH: 12
<212> TYPE: PRT
<213> ORGANISM: Artificial Sequence
<220> FEATURE:
<223> OTHER INFORMATION: HPC10
```

```
<400> SEQUENCE: 6

Gly Leu Asp His Leu Trp Trp Ser Ser Gln Thr Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: HPC3

<400> SEQUENCE: 7

Asn Pro Trp Asn Glu Met Trp Phe Gln Thr Ser Arg
1               5                   10

<210> SEQ ID NO 8
<211> LENGTH: 12
<212> TYPE: PRT
<213> ORGANISM: Artificial Sequence
<220> FEATURE:
<223> OTHER INFORMATION: HPC6

<400> SEQUENCE: 8

Trp Ala Asp Met Met Thr Ser Val Thr Pro Trp Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: HPC7

<400> SEQUENCE: 9

Ser Glu Phe Pro Arg Ser Trp Asp Met Glu Thr Asn
1               5                   10

<210> SEQ ID NO 10
<211> LENGTH: 12
<212> TYPE: PRT
<213> ORGANISM: Artificial Sequence
<220> FEATURE:
<223> OTHER INFORMATION: HPC8

<400> SEQUENCE: 10

Gln His Tyr Glu Thr Leu Ala Phe Arg Pro Lys His
1               5                   10

<210> SEQ ID NO 11
<211> LENGTH: 12
<212> TYPE: PRT
<213> ORGANISM: Artificial Sequence
<220> FEATURE:
<223> OTHER INFORMATION: HPC11

<400> SEQUENCE: 11

Ala Thr Tyr Asn Ser Val Asn Arg His Ser Ala Val
1               5                   10

<210> SEQ ID NO 12
<211> LENGTH: 20
<212> TYPE: DNA
<213> ORGANISM: Artificial Sequence
<220> FEATURE:
<223> OTHER INFORMATION: primer for pIII gene
```

```
<400> SEQUENCE: 12
ccctcatagt tagcgtaacg                                              20

<210> SEQ ID NO 13
<211> LENGTH: 12
<212> TYPE: PRT
<213> ORGANISM: Artificial Sequence
<220> FEATURE:
<223> OTHER INFORMATION: control peptide

<400> SEQUENCE: 13

Lys Ala Thr Glu Glu Gln Leu Lys Thr Val Met Glu
1               5                   10

<210> SEQ ID NO 14
<211> LENGTH: 5
<212> TYPE: PRT
<213> ORGANISM: Artificial Sequence
<220> FEATURE:
<223> OTHER INFORMATION: NPW-E motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 14

Asn Pro Trp Xaa Glu
1               5

<210> SEQ ID NO 15
<211> LENGTH: 5
<212> TYPE: PRT
<213> ORGANISM: Artificial Sequence
<220> FEATURE:
<223> OTHER INFORMATION: W-EMM motif
<220> FEATURE:
<221> NAME/KEY: misc_feature
<222> LOCATION: (2)..(2)
<223> OTHER INFORMATION: Xaa can be any naturally occurring amino acid

<400> SEQUENCE: 15

Trp Xaa Glu Met Met
1               5

<210> SEQ ID NO 16
<211> LENGTH: 5
<212> TYPE: PRT
<213> ORGANISM: Artificial Sequence
<220> FEATURE:
<223> OTHER INFORMATION: MHL-W motif
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Met His Leu Xaa Trp
1               5
```